United States Patent [19]

Lantzsch et al.

[11] Patent Number: 5,710,279

[45] Date of Patent: Jan. 20, 1998

[54] N-ACYLOXYALKYL-CARBOXAMIDES AND PROCESS FOR THEIR PREPARATION

[75] Inventors: Reinhard Lantzsch, Wuppertal; Werner Lindner, Köln, both of Germany

[73] Assignee: Bayer Aktiengesellschaft, Leverkusen, Germany

[21] Appl. No.: 708,441

[22] Filed: Sep. 5, 1996

Related U.S. Application Data

[62] Division of Ser. No. 393,960, Feb. 24, 1995, Pat. No. 5,599,940.

[30] Foreign Application Priority Data

Mar. 4, 1994 [DE] Germany .................. 44 07 182.5

[51] Int. Cl.[6] .................. C07C 69/63; C07C 69/02; C07D 213/55; C07D 333/24
[52] U.S. Cl. .................. 546/329; 549/74; 560/226; 560/227; 560/228; 560/229; 560/250; 560/253
[58] Field of Search .................. 546/329; 549/74; 560/226, 227, 228, 229, 250, 253

[56] References Cited

U.S. PATENT DOCUMENTS

| | | | |
|---|---|---|---|
| 2,980,688 | 4/1961 | Kamas | 548/191 |
| 3,317,603 | 5/1967 | Blance et al. | 564/215 |

FOREIGN PATENT DOCUMENTS

| | | |
|---|---|---|
| 0546418 | 6/1993 | European Pat. Off. . |
| 428700 | 12/1962 | Germany . |

OTHER PUBLICATIONS

H. Breederveld, Recueil Des Travaux Chimigues Des Pags--Bas, vol. 79, pp. 401-407, (1960).

Primary Examiner—Alan L. Rotman
Attorney, Agent, or Firm—Sprung Kramer Schaefer & Briscoe

[57] ABSTRACT

The invention provides novel N-acyloxyalkyl-carboxamides of the general formula (I):

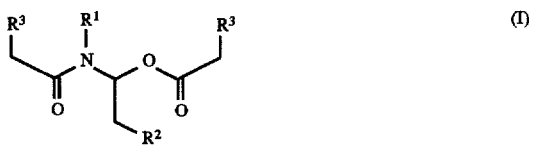

in which $R^1$ is alkyl, alkenyl, alkinyl, cycloalkyl, cycloalkylalkyl, arylalkyl or heteroarylalkyl, each of which is optionally substituted, $R^2$ is optionally substituted alkyl and $R^3$ is hydrogen, halogen or optionally substituted alkyl, in the isolated and pure form, and a process for their preparation.

1 Claim, No Drawings

N-ACYLOXYALKYL-CARBOXAMIDES AND PROCESS FOR THEIR PREPARATION

This application is a divisional, of application Ser. No. 08/393,960, filed on Feb. 24, 1995, now U.S. Pat. No. 5,599,940.

The invention relates to novel N-acyloxyalkyl-carboxamides which can be used as intermediates for the preparation of agrochemical or pharmaceutical active substances, and to a process for their preparation.

It is known from the literature that N-acyloxyalkyl-carboxamides cannot be isolated on account of their poor stability (cf. Recueil Trav. Chim. Pays Bas 79, 402; U.S. Pat. No. 3,317,603).

The present invention provides (1) novel N-acyloxyalkyl-carboxamides of the general formula (I):

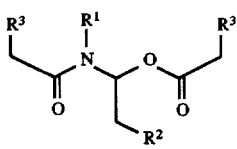

in which $R^1$ is alkyl, alkenyl, alkinyl, cycloalkyl, cycloalkylalkyl, arylalkyl or heteroarylalkyl, each of which is optionally substituted, $R^2$ is optionally substituted alkyl and $R^3$ is hydrogen, halogen or optionally substituted alkyl, in the isolated and pure form (purity at least 90% by weight), and (2) a process for the preparation of N-acyloxyalkyl-carboxamides of the general formula (I):

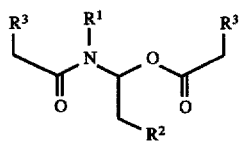

in which $R^1$ is alkyl, alkenyl, alkinyl, cycloalkyl, cycloalkylalkyl, arylalkyl or heteroarylalkyl, each of which is optionally substituted, $R^2$ is optionally substituted alkyl and $R^3$ is hydrogen, halogen or optionally substituted alkyl, characterized in that imines of the general formula (II):

in which $R^1$ and $R^2$ are as defined above, are reacted with anhydrides of the general formula (III):

$$(R^3—CH_2—CO)_2O \quad (III)$$

in which $R^3$ is as defined above, in the presence of a base and optionally in the presence of a diluent, at temperatures between −30° C. and +50° C. p In view of the state of the art cited above (Recueil Trav. Chim. Pays Bas 79, 402), it is to be regarded as extremely surprising that the process according to the invention makes it possible to obtain the N-acyloxyalkyl-carboxamides of the formula (I) as isolable products in high yields and in good quality. In subject to the state of the art, where the base is used in equimolar proportions or in excess, the base is used in less than equimolar proportions in the process according to the invention.

The conversion to corresponding enamides (below), which can be used as intermediates for agrochemicals and pharmaceutical active substances, is effected with substantially better yields than by known methods (cf. J. Chem. Soc. Perkin Trans. I 1984, 1173–1182). The process according to the invention thus represents a considerable enrichment of the state of the art.

The invention relates preferentially to novel N-acyloxyalkyl-carboxamides of the formula (I) to be prepared by the process according to the invention, in which formula $R^1$ is alkyl having 1 to 6 carbon atoms which is optionally substituted by halogen or $C_1$–$C_4$-alkoxy, alkenyl or alkinyl each having 3 to 6 carbon atoms, each of which is optionally substituted by halogen, cycloalkyl or cycloalkylalkyl each having 3 to 6 carbon atoms in the cycloalkyl moieties and optionally 1 to 4 carbon atoms in the alkyl moiety, each of which is optionally substituted by halogen or $C_1$–$C_4$-alkyl, or arylalkyl having 6 or 10 carbon atoms in the aryl moiety and 1-to 4 carbon atoms in the alkyl moiety, or heteroarylalkyl having 3 to 5 carbon atoms and 1 to 3 heteroatoms—especially nitrogen, oxygen or sulphur—in the heteroaryl moiety and 1 to 4 carbon atoms in the alkyl moiety, each of which is optionally substituted by halogen, $C_1$–$C_4$-alkyl or $C_1$–$C_4$-alkoxy, $R^2$ is alkyl having 1 to 6 carbon atoms which is optionally substituted by halogen or $C_1$–$C_4$-alkoxy, and $R^3$ is hydrogen, halogen or alkyl having 1 to 4 carbon atoms which is optionally substituted by halogen or $C_1$–$C_4$-alkoxy.

The invention relates in particular to novel N-acyloxyalkyl-carboxamides of the formula (I) to be prepared by the process according to the invention, in which formula $R^1$ is methyl, ethyl, n- or i-propyl or n-, i- or s-butyl, each of which is optionally substituted by fluorine, chlorine, methoxy or ethoxy, propenyl, butenyl, propinyl or butinyl, each of which is optionally substituted by fluorine, chlorine or bromine, cyclopropyl, cyclobutyl, cyclopentyl, cyclohexyl, cyclopropylmethyl, cyclobutylmethyl, cyclopentylmethyl or cyclohexylmethyl, each of which is optionally substituted by fluorine, chlorine, bromine, methyl, ethyl or n- or i-propyl, or benzyl, phenylethyl, phenylpropyl, naphthylmethyl, thienylmethyl or pyridylmethyl, each of which is optionally substituted by fluorine, chlorine, bromine, methyl, ethyl, n- or i-propyl, n-, i-, s- or t-butyl, methoxy or ethoxy, $R^2$ is methyl, ethyl, n- or i-propyl or n-, i-, s- or t-butyl, each of which is optionally substituted by fluorine, chlorine, methoxy or ethoxy, and $R^3$ is hydrogen, fluorine, chlorine, bromine or methyl, ethyl, n- or i-propyl or n-, i-, s- or t-butyl, each of which is optionally substituted by fluorine, chlorine, methoxy or ethoxy.

If, for example, N-methylpropanaldimine and acetic anhydride are used as the starting materials, the course of the reaction in processes according to the invention can be outlined by the following equation:

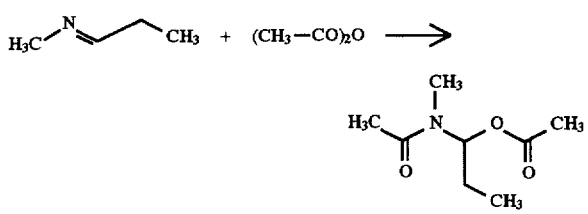

The imines to be used as starting materials in the process according to the invention for the preparation of the compounds of the general formula (I) are generally defined by the formula (II). In the formula (II), $R^1$ and $R^2$ preferably or particularly preferably have the meanings already indicated above, in connection with the description of the compounds of the formula (I), as preferred or particularly preferred meanings for $R^1$ and $R^2$.

The starting materials of the formula (II) are known and/or can be prepared by processes known per se (cf. EP-A 546418).

The anhydrides also to be used as starting materials in the process according to the invention are generally defined by the formula (III). In the formula (II), $R^3$ preferably or particularly preferably has the meaning already indicated above, in connection with the description of the compounds of the formula (I), as a preferred or particularly preferred meaning for $R^3$.

The starting materials of the formula (III) are known synthetic organic chemicals.

The process according to the invention is preferably carried out in the presence of a base, basic organic nitrogen compounds being particularly suitable for this purpose. These include for example trimethylamine, triethylamine, tripropylamine, tributylamine, dimethyl-butylamine, dibutylmethylamine, N,N-dimethyl-aniline, N,N-dimethyl-benzylamine, pyridine, picolines, dimethyl-pyridines, N-methyl-piperidine, N-methyl-morpholine, N,N-dimethylamino-pyridine and N,N-dimethyl-cyclohexylamine.

The process according to the invention is preferably carried out in the presence of a diluent, practically water-immiscible organic solvents being particularly suitable for this purpose. These include especially optionally halogenated aliphatic, alicyclic or aromatic hydrocarbons such as, for example, benzine, benzene, toluene, xylene, chlorobenzene, dichlorobenzene, petroleum ether, hexane, heptane, cyclohexane, methylcyclohexane, dichloromethane, chloroform and carbon tetrachloride; ethers such as, for example, diethyl ether, diisopropyl ether, t-butyl methyl ether, t-amyl methyl ether, dioxane, tetrahydrofuran and ethylene glycol dimethyl or diethyl ether; ketones such as, for example, methyl isopropyl ketone and methyl isobutyl ketone; and esters such as, for example, methyl, ethyl, n- or i-propyl and n-, i- and s-butyl acetate.

When the process according to the invention is carried out, the reaction temperatures can be varied within wide limits. In general, the operating temperatures are between −30° C. and +50° C., preferably between 0° C. and +30° C. and especially between 10° C. and 20° C.

The process according to the invention is generally carried out under normal pressure, but it is also possible to operate under increased or reduced pressure—generally between 0.1 bar and 10 bar.

To carry out the process according to the invention for the preparation of the compounds of the formula (I), 0.8 to 1.2 mol, preferably 1.00 to 1.10 mol, of anhydride of the formula (III) and optionally 0.1 to 1.0 mol, preferably 0.3 to 0.9 mol, of a base are generally used per mol of imine of the formula (II).

In a preferred embodiment of the process according to the invention, the anhydride of the formula (III) is placed in a suitable diluent, a solution of an imine of the formula (II) and a base in the same diluent is metered in at the lower end of the temperature range indicated above, and the reaction mixture is stirred until the reaction is complete.

The more volatile components—solvent and optionally base—are then distilled off under reduced pressure without allowing the temperature to exceed 50° C. The remaining residue then contains the product of the formula (I).

The N-acyloxyalkyl-carboxamides of the formula (I) to be prepared by the process according to the invention can be converted to corresponding enamides of the general formula (IV):

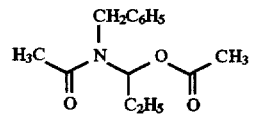

(IV)

in which $R^1$, $R^2$ and $R^3$ are as defined above, by pyrolysis, i.e. by heating to temperatures between 100° C. and 200° C., preferably between 120° C. and 150° C., under reduced pressure—generally between 0.1 mbar and 100 mbar, preferably between 1 mbar and 30 mbar (cf. the Preparatory Examples), said enamides being known as precursors for insecticides (cf. EP-A 546418).

PREPARATORY EXAMPLES

Example 1

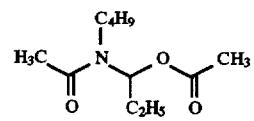

58.9 g (0.4 mol) of N-benzyl-propanaldimine are dissolved in 100 ml of toluene, and 25.4 g (0.2 mol) of N,N-dimethyl-cyclohexylamine are added. This solution is added dropwise to 40.8 g (0.4 mol) of acetic anhydride at 10°–15° C. The mixture is allowed to warm up to room temperature and the toluene and N,N-dimethyl-cyclohexylamine are distilled off under vacuum (initially 12 mbar, then 1–2 mbar) at a maximum of 50° C.

This gives a residue of 99.4 g of a clear oil consisting of N-benzyl-N-(1-acetoxypropyl)-acetamide, which corresponds to a yield of 99% of theory.

$^1$H NMR (CDCl$_3$, d): 0.9 ppm (t, CH$_3$), 1.65 ppm (s, CH$_3$), 1.8 ppm (m, CH$_2$), 2.4 ppm (s, CH$_3$), 4.35 and 4.85 (dd, CH$_2$), 6.25 ppm (t, CH), 7.1–7.4 ppm (m, C$_6$H$_5$).

Example 2

45.28 g (0.4 mol) of N-butyl-propanaldimine are dissolved in 100 ml of toluene, and 25.25 g (0.25 mol) of triethylamine are added. This solution is added dropwise to 40.8 g (0.4 mol) of acetic anhydride at 10°–15° C. The mixture is allowed to warm up to room temperature and the toluene and triethylamine are distilled off, initially under a water-jet vacuum and then under high vacuum (1–2 mbar), at a maximum of 40° C.

This gives 69 g of N-butyl-N-(1-acetoxypropyl)-acetamide as a clear colourless oil.

$n_D^{20} = 1.445$

By heating analogously to Example 2, N-butyl-N-propenyl-acetamide is obtained in a yield of 94% of theory (based on aldimine).

The compounds of the formula (I) listed in Table 1 below, for example, can also be prepared analogously to Examples 1 and 2 and in accordance with the general description of the process according to the invention.

TABLE 1

Examples of the compounds of the formula (I)

| Ex. no. | Structural formula | Refractive index |
|---|---|---|
| 3 | CH₃—N(CH(O—CO—CH₃)—CH₂CH₃)(CO—CH₃) | 1.441 |
| 4 | CH₂—CH₂—CH₂—N(CH(O—CO—CH₃)—CHCH₃)(CO—CH₃) | 1.458 |
| 5 | Cl—C₆H₄—CH₂—N(CH(O—CO—CH₃)—CH₂CH₃)(CO—CH₃) | 1.530 |
| 6 | C₆H₅—CH₂—N(CH(O—CO—C₂H₅)—CH₂CH₃)(CO—C₂H₅) | 1.512 |
| 7 | CH₃—N(CH(O—CO—CH₂Cl)—CH₂CH₃)(CO—CH₂Cl) | 1,498 |
| 8 | C₆H₅—CH₂—N(CH(O—CO—CH₂Cl)—C₂H₅)(CO—CH₂—Cl) | 1,516 |

ENAMIDES OF THE FORMULA (IV)

Example (IV-1)

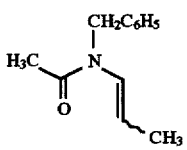

In a distillation apparatus, 74.8 g of the product of Example 1 are heated under reduced pressure (ca. 5 mbar) for 5 hours at 130° C. The acetic acid formed distils off. The residual N-benzyl-N-propenylacetamide weighs 56.7 g and has a content of 97% (HPLC).

The compounds of the formula (IV) listed in Table 2 below, for example, can also be prepared analogously to Example (IV-1).

TABLE 2

Examples of the compounds of the formula (IV)

| Ex. no. | Structural formula | Refractive index |
|---|---|---|
| IV-2 | CH₃—N(CH=CH—CH₃)(CO—CH₃) | 1.4794 |
| IV-3 | CH₂=CH—CH₂—N(CH=CH—CH₃)(CO—CH₃) | 1.4846 |
| IV-4 | Cl—C₆H₄—CH₂—N(CH=CH—CH₃)(CO—CH₃) | |
| IV-5 | C₆H₅—CH₂—N(CH=CH—CH₃)(CO—C₂H₅) | |
| IV-6 | CH₃—N(CH=CH—CH₃)(CO—CH₂Cl) | |
| IV-7 | C₆H₅—CH₂—N(CH=CH—CH₃)(CO—CH₂Cl) | |
| IV-8 | H₉C₄—N(CH=CH—CH₃)(CO—CH₃) | 1.4640 |

We claim:

1. A process for the preparation of an N-acyloxyalkyl-carboxamide of the formula (I):

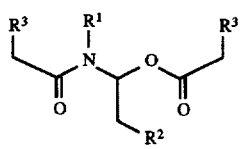
(I)

in which
- R¹ is alkyl, alkenyl, alkinyl, cycloalkyl, cycloalkylalkyl, arylalkyl or heteroarylalkyl, each of which is optionally substituted,
- R² is optionally substituted alkyl and
- R³ is hydrogen, halogen or optionally substituted alkyl, which comprises reacting an imine of the formula

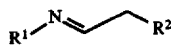
(II)

with an anhydride of the formula $(R^3-CH_2-CO)_2O$  (III)

in the presence of a base and optionally in the presence of a diluent, at a temperature between −30° C. and +50° C., and isolating the compound of the formula (I).